(12) United States Patent
Oftring et al.

(10) Patent No.: US 6,437,181 B1
(45) Date of Patent: Aug. 20, 2002

(54) METHOD FOR PRODUCING (S,S)-N,N'-ETHYLENEDIAMINEDISUCCINIC ACID, ANALOGOUS COMPOUNDS OR SALTS THEREOF

(75) Inventors: Alfred Oftring, Bad Dürkheim; Christian Ott, Speyer; Birgit Potthoff-Karl, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,530

(22) PCT Filed: Dec. 30, 1998

(86) PCT No.: PCT/EP98/08519

§ 371 (c)(1),
(2), (4) Date: Nov. 27, 2000

(87) PCT Pub. No.: WO99/35121

PCT Pub. Date: Jul. 15, 1999

(30) Foreign Application Priority Data

Jan. 8, 1998 (DE) .......................................... 198 00 437

(51) Int. Cl.[7] .............................................. C07C 229/00
(52) U.S. Cl. ...................................... 562/565; 562/566
(58) Field of Search .................................. 562/565, 566

(56) References Cited

U.S. PATENT DOCUMENTS 3,158,635 A * 11/1964 Kezerian et al. ............ 260/429
5,731,468 A * 3/1998 St. George et al. ......... 562/565

FOREIGN PATENT DOCUMENTS

| DE | 22 20 295 A | 11/1972 | |
|---|---|---|---|
| WO | 96 01803 | 1/1996 | |
| WO | 96 32371 A | 10/1996 | |
| WO | WO 9632371 | * 10/1996 | ................... 227/18 |

OTHER PUBLICATIONS

"The Synthesis and Reactions and beta–Substituted Ethyl Sulfates" Tomalia et al. J. of Heterocyclic Chem. vol. 9(4), pp. 891–894. (1982).*

* cited by examiner

Primary Examiner—Paul J. Killos
Assistant Examiner—Zachary Tucker
(74) Attorney, Agent, or Firm—Oblon, Spivak, McClelland, Maier & Neustadt, P.C.

(57) ABSTRACT

The invention describes a process for the preparation of (S,S)-N,N'-ethylenediaminedisuccinic acid or analogous compounds or their salts by reaction of L-aspartic acid, L-glutamic acid or L-cysteic acid with 1,2-bissulfooxyethane, 1,3,2-dioxathiolane 2,2-dioxide or mixtures thereof or 1,3-bissulfooxy-2-hydroxypropane in the presence of a base, and optional subsequent acidification with an acid.

Also described is a process for the preparation of (S,S)-N,N'-ethylenediaminedisuccinic acid or analogous compounds or their salts by reaction of N-(2-sulfooxyethyl)-L-aspartic acid or its salts with L-aspartic acid or corresponding compounds based on L-glutamic acid, L-cysteic acid and/or 1,3-bissulfooxy-2-hydroxypropane in the presence of a base, and optional subsequent acidification with an acid.

21 Claims, No Drawings

METHOD FOR PRODUCING (S,S)-N,N'-ETHYLENEDIAMINEDISUCCINIC ACID, ANALOGOUS COMPOUNDS OR SALTS THEREOF

The invention relates to a process for the preparation of (S,S)-N,N'-ethylenediaminedisuccinic acid ((S,S)-EDDS), analogous compounds or their salts. (S,S)-EDDS has the following formula:

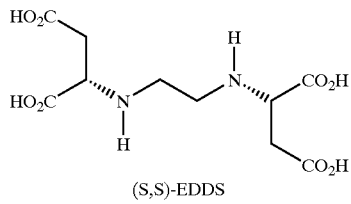

(S,S)-EDDS (S,S)-EDDS is used as a biodegradable complexing agent for alkaline earth metal ions and heavy metal ions.

Various processes for their preparation are known.

For example, (S,S)-EDDS can be prepared using microorganisms. Thus, alkylenediamines and fumaric acid can be reacted in the presence of Burkholderia sp., as is described in EP-A-0 731 171.

The preparation can also be carried out by reaction of L-aspartic acid with glyoxal in the presence of bases, and subsequent reduction with sodium borohydride. A process of this type is described, for example, in WO 96/32371.

The preparation can also be carried out by reaction of L-aspartic acid with glyoxal in the presence of bases, and subsequent reduction with sodium borohydride. A process of this type is described, for example, in WO 96/32371.

GB-A-2 299 809 describes the reaction of methyl L-aspartate with 1,2-dibromoethane.

According to WO 96/01801, the preparation of (S,S)-EDDS can be prepared by reaction of L-aspartic acid with 1,2-dibromoethane in water.

According to WO 94/28464, (rac)-EDDS is prepared by reaction of ethylenediamine and maleic acid.

The microbial processes for the preparation of (S,S)-EDDS are technically complex and produce the desired product only in a low yield. The other known processes likewise produce the desired product only in a low yield. The use of expensive chemicals is often necessary. The use of halogen-containing organic compounds always results in a certain content of organically bonded halogen (AOX). For environmental protection reasons, the formation of AOX should be avoided as far as possible.

It is an object of the present invention to provide a process for the preparation of (S,S)-EDDS and analogous compounds, which produces (S,S)-EDDS in a high yield starting from cost-effective, readily available starting materials in a straightforward process.

We have found that this object is achieved according to the invention by a process for the preparation of (S,S)-N,N'-ethylenediaminedisuccinic acid or analogous compounds or salts thereof by reaction of L-aspartic acid, L-glutamic acid or L-cysteic acid with 1,2-bissulfooxyethane, 1,3,2-dioxathiolane 2,2-dioxide, mixtures thereof or 1,3-bissulfooxy-2-hydroxypropane in the presence of a base, and optional subsequent acidification with an acid.

The object is further achieved according to the invention by a process for the preparation of (S,S)-N,N'-ethylenediaminedisuccinic acid or analogous compounds or salts thereof by reaction of N-(2-sulfooxyethyl)-L-aspartic acid or its salts with L-aspartic acid or corresponding compounds based on L-glutamic acid, L-cysteic acid and/or 1,3-bissulfooxy-2-hydroxypropane in the presence of a base, and optional subsequent acidification with an acid.

The invention further relates to a process for the preparation of N-(2-sulfooxy-ethyl)-L-aspartic acid or analogous compounds or salts thereof by reaction of L-aspartic acid, L-glutamic acid or L-cysteic acid with an equimolar amount of 1,2-bissulfooxyethane, 1,3,2-dioxathiolane 2,2-dioxide or mixtures thereof or 1,3-bissulfooxy-2-hydroxypropane in the presence of a base, and optional subsequent acidification with an acid.

According to the invention, it has been found that the preparation of (S,S)-EDDS by reaction of L-aspartic acid with ethylene glycol disulfuric acid (1,2-bis-sulfooxyethane, CAS: 6914-91-6) can take place in accordance with the following reaction scheme:

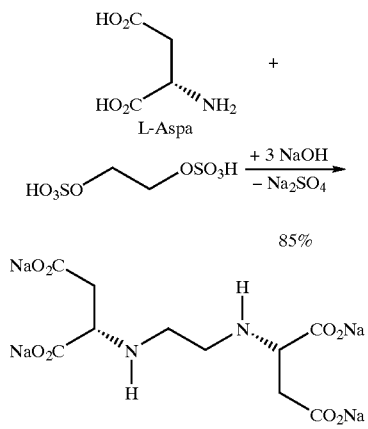

1,2-Bissulfooxyethane can be obtained by reaction of ethylene glycol with sulfur trioxide, chlorosulfonic acid, sulfuric anhydride or sulfuric acid. The synthesis is described, for example, in J. Prakt. Chem. 1879, 20, 2. The reaction of sulfur trioxide with ethylene glycol is described, for example, in J. Am. Chem. Soc. 1954, 76, 5361.

Instead of 1,2-bissulfooxyethane, it is also possible to use the cyclic glycol sulfate (1,3,2-dioxathiolane 2,2-dioxide, CAS: 1072-53-3). Glycol sulfate can be prepared, for example, by the process described in DE-A-20 40 503. The reaction takes place in accordance with the following scheme:

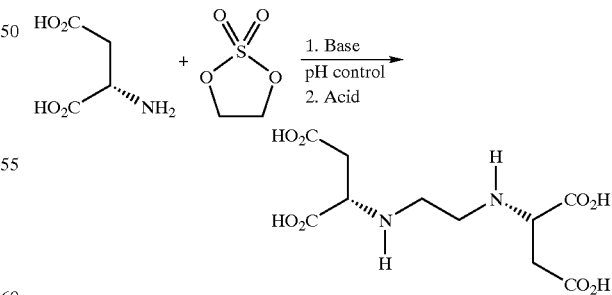

Instead of 1,2-bissulfooxyethane or 1,3,2-dioxathiolane 2,2-dioxide, it is also possible to use a mixture of both compounds. The reaction is carried out using 2 equivalents of L-aspartic acid. Furthermore, the reaction can also be carried out sequentially. For this, L-aspartic acid is firstly reacted with an equivalent of 1,2-bissulfooxyethane or 1,3,2- dioxathiolane 2,2-dioxide or mixtures thereof to give N-(2-sulfooxyethyl)-L-aspartic acid or its salts. This compound is then reacted with an equivalent of L-aspartic acid in the presence of bases to give (S,S)-EDDS in accordance with the following scheme:

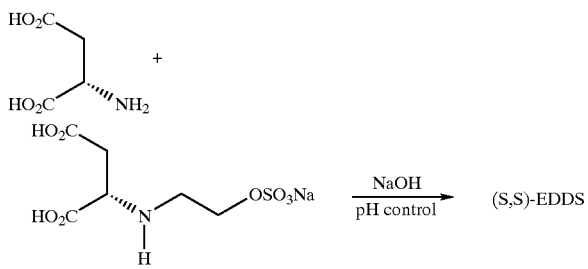

The bases used in the reactions can be any suitable bases. Examples are alkali metal and alkaline earth metal hydroxides, alkali metal and alkaline earth metal carbonates, tertiary amines or ammonia, and mixtures thereof. Preference is given to using sodium hydroxide, sodium carbonate, potassium hydroxide, potassium carbonate or calcium hydroxide. If ammonia is used, any ammonium sulfate which forms can be reconverted into ammonia and sulfuric acid in a simple manner.

During the reaction, the pH is preferably maintained in the range from 7 to 13, preferably from 7 to 11, particularly preferably from 8 to 10. After the reaction, the product can be acidified with an acid. Suitable acids are, for example, organic carboxylic acids, such as acetic acid, or inorganic acids, such as sulfuric acid. If the product is completely acidified, then free (S,S)-EDDS is obtained. This can be isolated by mechanical separation (filtration) since it precipitates out of the reaction mixture. In this case, all carboxyl groups in the (S,S)-EDDS are in protonated form. By omitting the acidification with an acid or acidification with a smaller amount of acid, salts of (S,S)-EDDS can be obtained in which 1 to 4 of the carboxyl groups are present in salt form. Thus, mono-, di-, tri- or tetra-salts, for example, can be prepared. In the salts, the counterion present is the ion of the corresponding base used. If sodium carbonate or sodium hydroxide are used, then mono-, di-, tri- and tetra-sodium salts of (S,S)-EDDS can be obtained. If the corresponding potassium compounds are used, the corresponding potassium salts are obtained. In product mixtures, on average, uneven values for the number of salt groups in the molecule can also be obtained.

If calcium hydroxide is used as the base, the corresponding calcium salts are firstly obtained, which can be converted into the sodium salts by adding sodium carbonate and separating off the sparingly soluble calcium carbonate.

The reaction is preferably carried out in aqueous solution. A preferred method involves suspending L-aspartic acid in water and adding base until the desired pH is established. Then, 1,2-bissulfooxyethane, 1,3,2-dioxathiolane 2,2-dioxide or mixtures thereof are gradually introduced into the reaction mixture. During the reaction, the reaction temperature should preferably not exceed 50° C., particularly preferably 30° C., in particular 25° C. During the addition, the pH is maintained at the desired value by adding base. When the addition is complete, the reaction mixture is preferably heated to a temperature in the range from 30 to 100° C., particularly preferably 60 to 100° C., in particular under reflux. The progress of the reaction can be monitored, for example, by HPLC (High Performance Liquid Chromatography). As soon as no further decrease in the amount of L-aspartic acid can be detected, the reaction mixture is cooled and worked up. For example, the reaction mixture can be rendered acidic using sulfuric acid, and the precipitated (S,S)-EDDS can be separated off mechanically, for example by filtration or centrifugation. When the reaction is complete, the reaction mixture can also be spray-dried without acidification. In this process a mixture of (S,S)-EDDS tetrasodium salt, L-aspartic acid disodium salt, ethylene glycol and sodium sulfate is obtained if the base used was sodium hydroxide solution. If other bases are used, the corresponding salts are obtained.

Corresponding reactions are possible with L-glutamic acid, L-cysteic acid, 1,2-bissulfooxyethane and 1,3-bissulfooxy-2-hydroxypropane. In each case, S,S-configurations are obtained, e.g. (S,S)-EDDG and (S,S)-HPDDS, i.e. (S,S)-ethylenediamineglutamic acid and hydropropylene-1,3-diaminodisuccinic acid.

The invention is additionally illustrated below by reference to examples.

EXAMPLES

Example 1

(S,S)-N,N'-Ethylenediaminedisuccinic acid 66.6 g (0.50 mol) of L-aspartic acid were suspended in 200 ml of water at room temperature in a 1 l stirred apparatus fitted with reflux condenser. 50% strength sodium hydroxide solution was used to establish a pH of from 9 to 10. 111 g (0.50 mol) of 1,2-bissulfooxyethane were slowly introduced using a solids funnel (screw funnel) such that the internal temperature did not exceed 25° C. During the addition, the pH was maintained at 9 to 10 using 50% strength sodium hydroxide solution.

When the addition was complete, the reaction mixture was heated at 100° C. for 4 h. The reaction was monitored by means of HPLC.

As soon as no further decrease in L-aspartic acid could be detected, the mixture was rendered acid using 60% strength sulfuric acid, and the precipitated (S,S)-N,N'-ethylenediaminedisuccinic acid was filtered off with suction. It was purified by subsequently washing with cold water. Yield: 57.6 g (79%) of (S,S)-N,N'-ethylenediaminedisuccinic acid.

Example 2

(S,S)-N,N'-Ethylenediaminedisuccinic acid tetrasodium salt 133 g (1 mol) of L-aspartic acid were suspended in 400 ml of water at room temperature in a 1 l stirred apparatus fitted with reflux condenser. 50% strength sodium hydroxide solution was used to establish a pH of from 9 to 10. 222 g (1 mol) of 1,2-bissulfooxyethane were slowly introduced using a solids funnel (screw funnel) such that the internal temperature did not exceed 25° C. During the addition, the pH was maintained at 9 to 10 using 50% strength sodium hydroxide solution.

When the addition was complete, the reaction mixture was heated at 100° C. for 4 h. The reaction was monitored by means of HPLC.

As soon as no further decrease in the amounts of L-aspartic acid could be detected, the reaction mixture was spray-dried. This gives a mixture of 160 g (31% by weight, corresponds to a chemical yield of 84%) of (S,S)-N,N'-ethylenediaminedisuccinic acid tetrasodium salt, 28 g of L-aspartic acid disodium salt, 36 g of ethylene glycol and 284 g of sodium sulfate.

We claim:

1. A method for preparing a (S,S)-N,N' alkyldiamine of formula $R^1N(H)R^3N(H)R^2$, or a salt thereof, where $R^1$ and $R^2$ are $C(H)(COOH)(CH_2COOH)$, $C(H)(COOH)(CH_2CH_2COOH)$, or $C(H)(COOH)(CH_2SO_3H)$ and $R^3$ is $CH_2CH_2$ or $CH_2C(H)(OH)CH_2$, comprising reacting a compound of the formula $RNH_2$ or a salt thereof where $R=R^1$ or $R^2$ with 1,2-bissulfooxyethane, 1,3,2-dioxathiolane 2,2-dioxide, or 1,2-bissulfooxy-2-hydroxypropane in the presence of a base.

2. The method of claim 1, further comprising acidifying the reaction product of $RNH_2$ and 1,2-bissulfooxyethane, 1,3,2-dioxathiolane 2,2-dioxide, or 1,2-bissulfooxy-2-hydroxypropane.

3. The method of claim 1, comprising preparing $R^1N(H)R^3N(H)R^2$ where one to four of the carboxylic groups in $R^1$ and $R^2$ are present as a salt.

4. The method of claim 1, wherein said base is selected from the group consisting of an alkali metal hydroxide, an alkali metal carbonate, a tertiary amine, ammonia, or a mixture thereof.

5. The method of claim 1, further comprising maintaining the pH in the range of 8 to 11 during reaction.

6. The method of claim 1, further comprising spray drying the product of formula $R^1N(H)R^3N(H)R^2$.

7. The method of claim 1, further comprising mechanically isolating the product of formula $R^1N(H)R^3N(H)R^2$ after acidification.

8. A method for preparing a (S,S)-N,N' alkyldiamine of formula $R^1N(H)R^3N(H)R^2$ where $R^1$ and $R^2$ are $C(H)(COOH)(CH_2COOH)$, $C(H)(COOH)(CH_2CH_2COOH)$, or $C(H)(COOH)(CH_2SO_3H)$ and $R^3$ is $CH_2CH_2$ or $CH_2C(H)(OH)CH_2$ comprising reacting a compound of the formula $RNH_2$ or a salt thereof, where $R=R^1$ or $R^2$ are as described above, with an N-(sulfooxyalkyl) of the formula $R^1N(H)R^3X$ where $R^1$ and $R^3$ are as described above and X is $OSO_3Na$ or $OSO_3H$, in the presence of base.

9. The method of claim 8, further comprising acidifying the reaction product of $RNH_2$ and N-(sulfooxyalkyls) of formula $R^1N(H)R^3X$.

10. The method of claim 8, comprising preparing $R^1N(H)R^3N(H)R^2$ where one to four of the carboxylic groups in $R^1$ and $R^2$ are present as a salt.

11. The method of claim 8, wherein said base is selected from the group consisting of an alkali metal hydroxide, an alkali metal carbonate, a tertiary amine, ammonia, or a mixture thereof.

12. The method of claim 8, further comprising maintaining the pH in the range of 8 to 11 during reaction.

13. The method of claim 8, further comprising spray drying the product of formula $R^1N(H)R^3N(H)R^2$.

14. The method of claim 8, further comprising mechanically isolating the product of formula $R^1N(H)R^3N(H)R^2$ after acidification.

15. A method for preparing a N-(sulfooxyalkyl) of formula $R^1N(H)R^3X$, or a salt thereof, where $R^1$ is $C(H)(COOH)(CH_2COOH)$, $C(H)(COOH)(CH_2CH_2COOH)$, or $C(H)(COOH)(CH_2SO_3H)$ and $R^3$ is $CH_2CH_2$ or $CH_2C(H)(OH)CH_2$ and X is $OSO_3Na$ or $OSO_3H$, comprising reacting a compound of formula $RNH_2$ or a salt thereof, where $R=R^1$ or $R^2$ is described above, with an equimolar amount of 1,2-bissulfooxyethane, 1,3,2-dioxathiolane 2,2-dioxide, or mixtures thereof in the presence of base, or with an equimolar amount of 1,3-bissulfooxy-2-hydroxypropane in the presence of a base.

16. The method of claim 15, further comprising acidifying the reaction product of $RNH_2$ and a sulfooxyalkyl.

17. The method of claim 15, comprising preparing $R^1N(H)R^3N(H)R^2$ where one to four of the carboxylic groups in $R^1$ and $R^2$ are present as a salt.

18. The method of claim 15, wherein said base is selected from the group consisting of an alkali metal hydroxide, an alkali metal carbonate, a tertiary amine, ammonia, or mixtures thereof.

19. The method of claim 15, further comprising maintaining the pH in the range of 8 to 11 during reaction.

20. The method of claim 15, further comprising spray drying the product of formula $R^1N(H)R^3X$.

21. The method of claim 15, further comprising mechanically isolating the N-(sulfooxyalkyl) of formula $R^1N(H)R^3X$ after acidification.

* * * * *